(12) United States Patent
Kamino et al.

(10) Patent No.: US 9,499,900 B2
(45) Date of Patent: Nov. 22, 2016

(54) ION MILLING DEVICE

(71) Applicant: Hitachi High-Technologies Corporation, Minato-ku, Tokyo (JP)

(72) Inventors: Atsushi Kamino, Tokyo (JP); Hisayuki Takasu, Tokyo (JP); Hirobumi Muto, Tokyo (JP); Toru Iwaya, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 97 days.

(21) Appl. No.: 14/379,805

(22) PCT Filed: Feb. 18, 2013

(86) PCT No.: PCT/JP2013/053794
§ 371 (c)(1),
(2) Date: Aug. 20, 2014

(87) PCT Pub. No.: WO2013/145926
PCT Pub. Date: Oct. 3, 2013

(65) Prior Publication Data
US 2015/0008121 A1    Jan. 8, 2015

(30) Foreign Application Priority Data
Mar. 26, 2012 (JP) ................. 2012-068582

(51) Int. Cl.
*C23C 14/30* (2006.01)
*G01N 1/32* (2006.01)
*H01J 37/305* (2006.01)
*H01J 37/20* (2006.01)
*H01J 37/30* (2006.01)

(52) U.S. Cl.
CPC ............... *C23C 14/30* (2013.01); *G01N 1/32* (2013.01); *H01J 37/20* (2013.01); *H01J 37/30* (2013.01); *H01J 37/3053* (2013.01); *H01J 37/3056* (2013.01); *H01J 2237/317* (2013.01); *H01J 2237/31745* (2013.01); *H01J 2237/31749* (2013.01); *H01J 2237/334* (2013.01)

(58) Field of Classification Search
CPC .......... C23C 14/30; G01N 1/28; G01N 1/32; H01J 37/20; H01J 37/30; H01J 37/3053; H01J 37/3056; H01J 2237/317; H01J 2237/31745; H01J 2237/31749; H01J 2237/334
USPC ........................................ 204/298.36, 192.34
See application file for complete search history.

(56) References Cited

U.S. PATENT DOCUMENTS

2010/0018858 A1 * 1/2010 Seki ................. H01J 37/09
204/298.36

FOREIGN PATENT DOCUMENTS

JP    2009-245783 A    10/2009

OTHER PUBLICATIONS

Machine Translation JP 2009-245783 dated Oct. 2009.*

*Primary Examiner* — Rodney McDonald
(74) *Attorney, Agent, or Firm* — Miles & Stockbridge P.C.

(57) ABSTRACT

The present invention advantageously provides an ion milling device that can set a high-precision processing area with a simple structure. The ion milling device includes a sample holder that holds a sample and a mask partially restricting irradiation of the sample with an ion beam. The sample holder includes a first contact surface that contacts an end surface of the sample located on a passing orbit side of the ion beam, and a second contact surface that contacts an end surface of the mask so that the mask is located at a position spaced apart from the ion beam more than the first contact surface.

8 Claims, 5 Drawing Sheets

ION MILLING DEVICE

TECHNICAL FIELD

The present invention relates to an ion milling device, and particularly to a sample holding table for the ion milling device that produces a sample for an electron scanning microscope, and an ion milling device that processes the sample placed on the sample holding table.

BACKGROUND ART

The ion milling device is a device that smoothly mills a sample without any stress with the use of a physical sputtering phenomenon in which ions of argon or the like generated within an anode are accelerated to about 10 kV or lower (in order to reduce a damage on the sample), and the sample is irradiated with the ions not converged to sputter sample atoms from a sample surface.

The amount of sample milled by irradiating the sample with an ion beam depends on composition of the sample, an irradiation angle of the ion beam, a crystal orientation, or an acceleration voltage of the ion. However, when the sample is set so that the irradiation angle of the ion beam becomes 90 degrees, a difference in the milled amount depending on the composition of the sample can be reduced, and a multi-layer film of multiple composition can be also smoothly processed.

In this situation, in the irradiation of the sample with the ion beam, in order to prevent a position other than an ion milling target position from being irradiated with the ion beam, a plate (hereinafter also called "shield" or "mask") for blocking the ion beam is arranged in the ion beam irradiation direction (note: ion source side=ion gun side) of the sample at a processing target position. The sample is exposed from the shield by several hundred microns or lower, and irradiated with the ion beam, and an exposed sample portion is physically sputtered, and milled, to thereby obtain a smooth sample surface.

PTL 1 discloses that a micrometer for regulating a mask position is disposed for the purpose of accurately setting a processing area (exposed area of the sample to the ion beam).

SUMMARY OF INVENTION

Embodiments of the present invention advantageously provide an ion milling device including: an ion source for irradiating a sample with an ion beam; and a sample stage disposed within a vacuum chamber for the sample to be irradiated with the ion beam, in which a sample holder holds the sample, and a mask partially limits irradiation of the sample with the ion beam.

The sample holder includes a first contact surface that contacts an end surface of the sample located on a passing orbit side of the ion beam, and a second contact surface that contacts an end surface of the mask so that the mask is located at a position spaced apart from the ion beam more than the first contact surface.

DESCRIPTION OF EMBODIMENTS

Technical Problem

Figure 1:
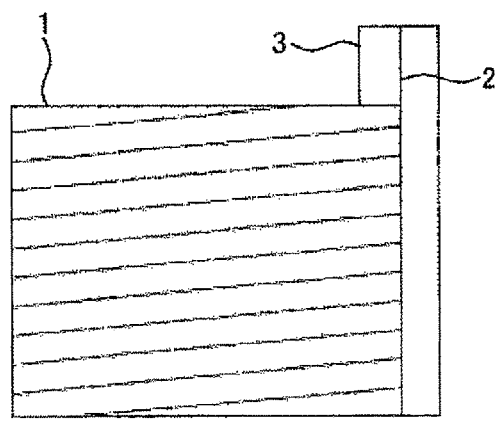
FIG. 1 is a diagram illustrating an example of a sample table.

The sample to be subjected to ion milling is, for example, an observation sample by an electron microscope, and frequently very fine. The micrometer disclosed in PTL 1 is a tool effective in setting the processing area of such a fine sample. However, its structure becomes very complicated more as the target sample is finer. Further, because a sample holder becomes larger by microscale, a work within a limited space is difficult.

An ion milling device having a sample holder intended to set a high-precision processing area with a simple structure will be described below.

Advantageous Effects of Invention

According to the above configuration, the ion milling device having the sample holder intended to set a high-precision processing area with a simple structure can be provided.

As the amount of exposure (processing area) of a sample to anion beam in an ion milling device, there is a regulation method of regulating an intended amount of exposure by a precision fine movement mechanism such as a micrometer having at least one direction (one axis) in which the sample fitted onto the sample table and the shield arranged on an ion beam irradiation side of the sample are made independent from each other. However, a structure of a sample holder is complicated, the number of components increases, and external diameters are large, the sample cannot be observed (hereinafter called "sharing of the sample holder", etc.) by an electron scanning microscope while the sample is kept to be installed in the sample holder, and the manufacturing costs are high.

For that reason, in this embodiment, a sample holder structure is proposed in which a protrusion structure for holding an end surface of a sample processing surface, and a protrusion structure for holding a shield end surface are used for a surface of a sample table for fixing the sample on which the sample is placed, and relative position of the respective protrusion structures is predetermined in dimension so that the irradiation of the sample with the ion beam has an intended sample exposure amount.

A groove is formed in apart of the protrusion structure for holding the sample processing surface end surface of the sample table, and the sample holder is not directly irradiated with the ion beam that penetrates through the sample. With this configuration, the shield can be fixed directly to the sample holder, and the sample can be arranged between the shield and the sample table.

Also, an outer shape of the sample holder is set to, for example, about φ70 mm or lower so that the sample holder can be shared with the electron scanning microscope. As a result, a cap for sealing the sample placed on the sample table from an outside air can be installed on the sample holder depending on the intended use. Also, in this case, the sample holder outer shape including the cap is set to a dimension of about φ70 mm×60 mm in height or lower so that the sample holder can be shared with the electron scanning microscope.

According to the configuration described above, it is unnecessary to regulate the shield by the precision fine movement mechanism such as the micrometer having the independent one direction (one axis) or more, the structure is simple, the number of components is small, and the external dimension can be reduced. Also, the electron scanning microscope and the sample holder can be shared while the sample is kept to be placed on the sample holder.

Figure 2:
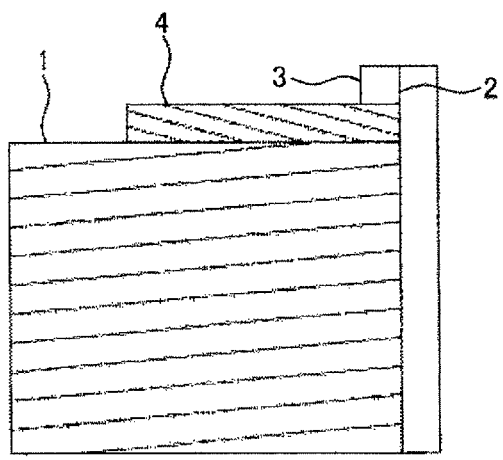
FIG. 2 is a diagram illustrating an example in which a sample is fitted onto the sample table.
Figure 3:
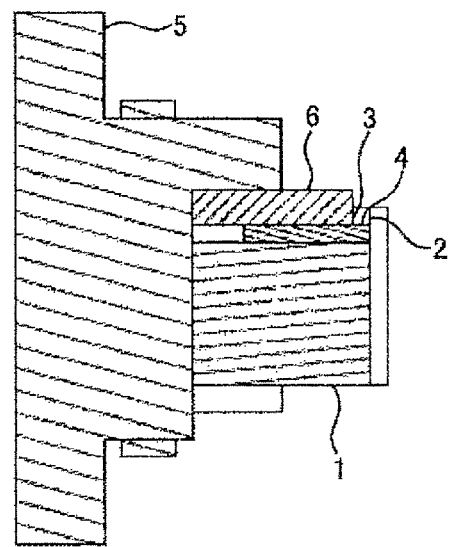
FIG. 3 is a diagram illustrating one example of a sample holder in which the sample and a shield (mask) are fitted onto the sample table.

A more specific structure will be described below. FIG. 1 is a diagram illustrating an example of the sample holder of the sample to be ion-milled. A sample end surface placement protrusion 2 and a shield end surface installation protrusion 3 for enabling precise positioning of a sample end surface are disposed on a sample table 1 in advance. An example in which a sample 4 is placed on the sample table 1 is illustrated in FIG. 2. An end surface of the sample 4 is placed in close contact with the sample end surface placement protrusion 2 of the sample table 1. An example of the shield installation after the sample 4 has been placed on the sample table 1 is illustrated in FIG. 3. After the sample 4 has been placed on the sample table 1, the sample table 1 is fixed to a sample holder 5 so that an end surface of a shield 6 installed on the sample holder 5 in advance comes in close contact with the shield end surface installation protrusion of the sample table 1.

A relative position of the protrusion structure is predetermined in dimension so that the irradiation of the sample with the ion beam becomes an intended sample exposure amount, as a result of which the sample can be placed with various sample exposure amounts. Also, because the sample exposure amount is predetermined, there is no need to move the shield. Further, there is no need to fix the sample to the sample table by a conductive tape or paste.

As described above, the first embodiment has a feature that the sample is placed with a given sample exposure amount without any provision of the fine movement mechanism of the independent shield of the sample holder or the sample stage in the ion milling device.

Figure 4:
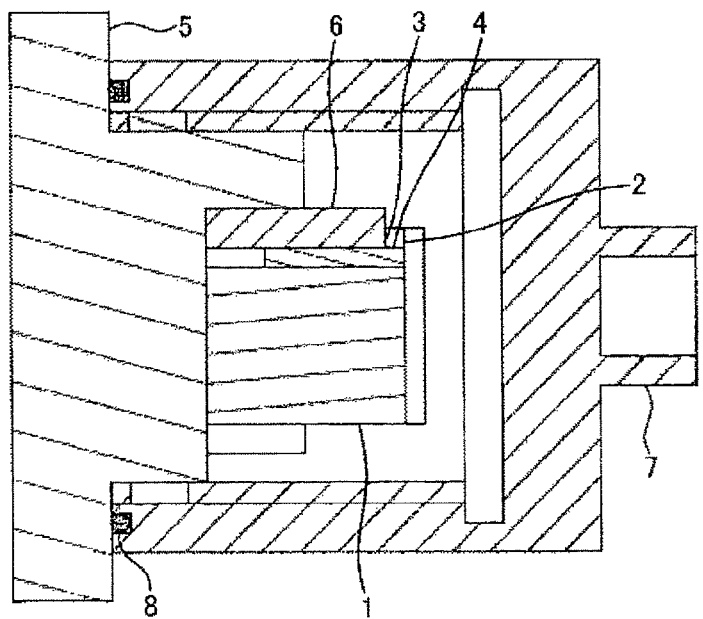
FIG. 4 is a diagram illustrating another example of the sample holder.

Subsequently, a second embodiment will be described with reference to FIG. 4. An example for sealing the sample holder 5 from the outside air is illustrated in FIG. 4. The sample holder 5 has a structure for mounting a cap 7 thereon, and a seal material 8 is incorporated into the cap 7 so that an interior of the sample holder 5 can be sealed from the outside air by the aid of the seal material 8. The cap 7 is removed in a sample chamber or a sample exchange chamber which is evacuated in the ion milling device or the electron scanning microscope whereby the sample can be processed and the sample can be observed without bringing the sample in contact with the outside air.

Figure 6:
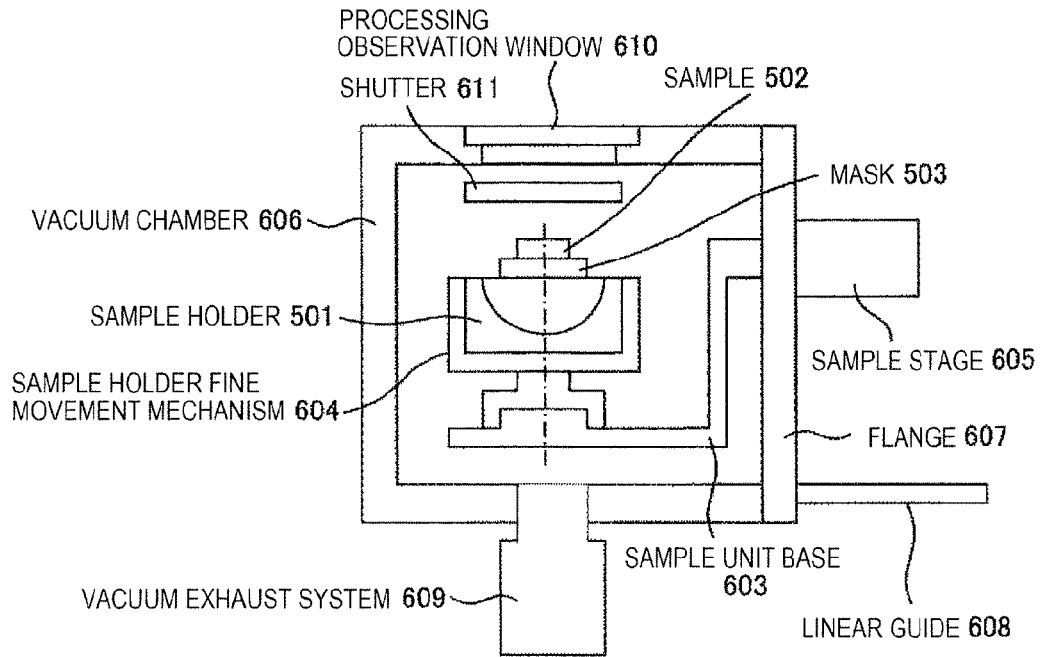
FIG. 6 is a diagram illustrating an outline of an ion milling device (side plan view).
Figure 7:
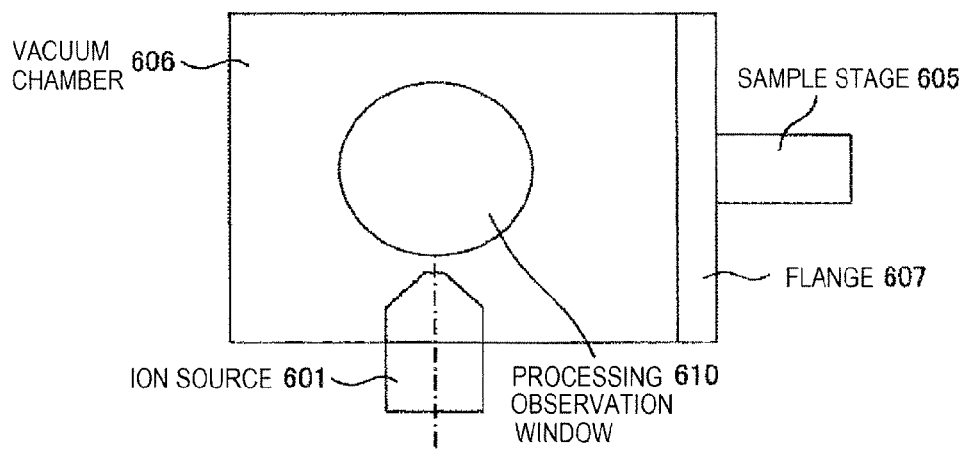
FIG. 7 is a diagram illustrating the outline of the ion milling device (top view).

FIGS. 6 and 7 illustrate the configuration of the ion milling device. An ion source 601 and a sample stage 605 are installed on side surfaces of a vacuum chamber 606. FIG. 6 is a side view, and FIG. 7 is a top view.

A sample holder fine movement mechanism 604 is mounted on a sample unit base 603. In a mounting method, a lower surface of the sample holder fine movement mechanism 604 is brought into contact with an upper surface of the sample unit base 603, and fixed by a screw or the like. The sample holder fine movement mechanism 604 is configured to be rotationally tilted at an arbitrary angle with respect to an optical axis (a direction perpendicular to a paper plane in FIG. 6) of the ion beam, a rotational tilt direction and a tilt angle are controlled by a control device not shown. The sample holder fine movement mechanism 604 is rotationally tilted so that a sample 502 placed on the sample holder fine movement mechanism 604 can be set at a given angle with respect to the optical axis of the ion beam. Further, the sample stage 605 is disposed to tilt a sample holder 501 in a direction parallel to the paper plane, which is perpendicular to a rotating axis of a tilt rotary motion, in addition to the tilt rotary motion. The tilting movement (tilt with a rotating shaft indicated by a dashed line in FIG. 6) of the sample holder fine movement mechanism 604 is mainly configured to continuously conduct the tilting movement in a section processing mode for processing a section of the sample. Also, the sample holder fine movement mechanism 604 is configured to be movable from front to back and from side to side in a direction perpendicular to the optical axis of the ion beam, that is, in an X-direction and a Y-direction.

The sample unit base 603 is arranged through the sample stage 605 (rotating mechanism) mounted on a flange 607 serving as a part of a container wall of the vacuum chamber 606. When the flange 607 is pulled out along a linear guide 608, and the vacuum chamber 606 is opened to an atmospheric state, the sample unit base 603 is pulled out to an external of the vacuum chamber. In this way, a sample stage pull-out mechanism is configured. During ion beam processing, the flange 607 is closed, and evacuation is conducted by a vacuum exhaust system 609.

FIGS. 6 and 7 illustrate a configuration of the ion milling device that can conduct both of cross-section milling and plane milling. A processing observation window 610 and an openable shutter 611 are disposed in an upper surface of the vacuum chamber 606. The shutter 611 is installed for preventing sputtered particle from being deposited on the processing observation window 610. The vacuum chamber 606 is formed into a boxed-shape that forms a space for forming a normal vacuum atmosphere, or formed into a shape based on the box. The observation window is disposed above the box (a direction opposite to a direction of a gravitational field under a gravitational environment), and the ion source is disposed on a side wall of the box (a plane adjacent to the upper surface of the box in a direction perpendicular to the direction of the gravitational field). That is, the processing observation window is disposed in a wall surface of the vacuum chamber in a direction orthogonal to the tilt axis of the sample stage and an plane including an irradiation orbit of the ion beam. As will be described later, aside from the provision of a vacuum-sealable window, an optical microscope or an electron microscope can be installed in the processing observation window opening.

Figure 8:
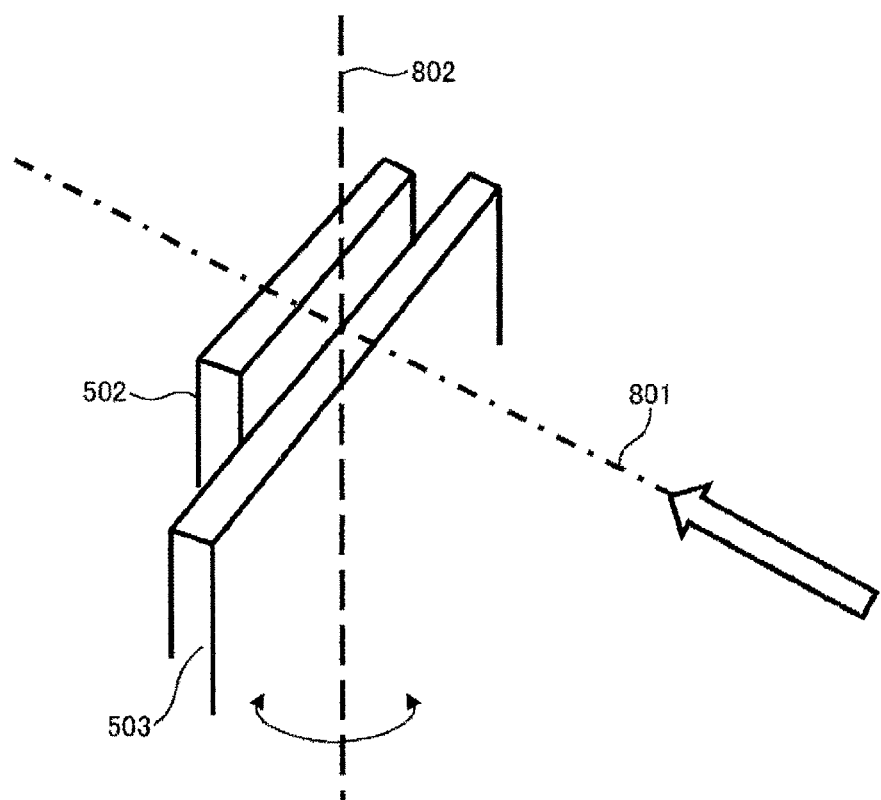
FIG. 8 is a diagram illustrating a positional relationship among an ion beam trajectory, the sample, and a mask during ion milling.

FIG. 8 is a diagram illustrating a positional relationship among an ion beam optical axis 801, the sample 502, and a mask 503 during cross-sectional processing. A rotating axis 802 corresponds to a dashed line in FIG. 6. The sample holder fine movement mechanism 604 conducts a continuous tilting movement with the rotating axis 802 as a center, and irradiates the sample with the ion beam in that state to conduct the cross-section processing.

Figure 5:
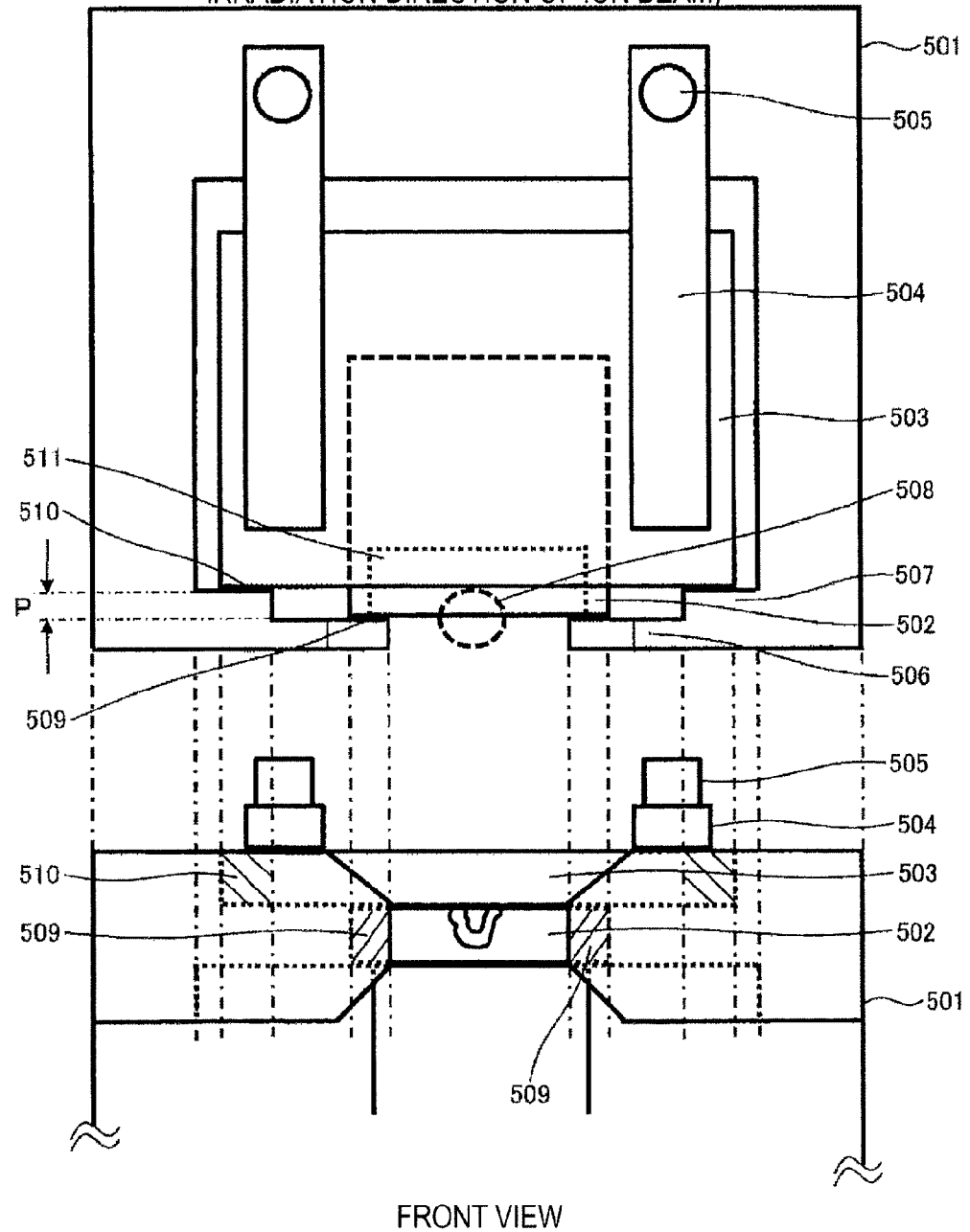
FIG. 5 is an illustrative view of the details of the sample holder.

An outline of the sample holder 501 mounted on the sample holder fine movement mechanism 604 will be described with reference to FIG. 5. In FIG. 5, a flange portion of the sample holder 5 in FIG. 4 is omitted. Also, when the sample holder 501 is really fitted to the sample holder fine movement mechanism 604, anion beam irradiation portion 508 is located to the top. The sample holder 501 is fixed to push the sample 502 to be ion-milled and the mask 503 which is a shield material against the sample holder 501. Mask fixing knobs 505 are threaded, and the knobs are rotated to press mask pressing members 504 downward.

The sample 502 is located to be partially exposed from the mask 503 when viewed from an ion beam irradiation direction, and the ion beam is applied to the ion beam irradiation portion 508 to process the cross-section of the sample.

In this example, the sample holder 501 includes a sample contact portion 506 and a mask contact portion 507. Contact surfaces 509 (first contact surface) with the sample are formed on an ion beam passing orbit center side more than contact surfaces 510 (second contact surface) with the mask so that the sample 502 is located closer to the ion beam optical axis center than the ion beam passing orbit side end surface of the mask 503. A space between the two contact surfaces 509, 510 and the sample configures an ion beam passing opening, and a gap is formed between the two contact surfaces 509, 510 for the purpose of ensuring the passing opening of the ion beam while contacting with the ends of the sample 502 and the mask 503. Also, an opening 511 (groove) is formed in the sample table on which the sample 502 is placed so that the sample 502 is not directly irradiated with the ion beam.

With the above configuration in which the opening through which the ion beam passes is ensured while providing the respective regions that contact with the end surface of the sample which is irradiated with the ion beam, and the end surface of the mask which is irradiated with the ion beam, the mask and the sample can be installed without conducting any precise positional regulation. In particular, in this embodiment, a gap P is formed between the contact surfaces 509 of the sample and the contact surface 510 of the mask in a direction perpendicular to the irradiation direction of the ion beam, and the processing area as large as the gap P can be set without requiring the precise regulation.

REFERENCE SIGNS LIST

501 sample holder
502 sample
503 mask
504 mask pressing member
505 mask fixing knob
506 sample contact portion
507 mask contact portion
508 ion beam irradiation portion
509, 510 contact surface

The invention claimed is:

1. An ion milling device comprising:
  an ion source for irradiating an upper surface of a sample with an ion beam having an optical axis, the sample further comprising a lower surface and a plurality of side surfaces;
  a sample stage disposed within a vacuum chamber for the sample to be irradiated with the ion beam;
  a sample holder, to hold the sample, including a first contact surface and a second contact surface; and
  a mask to partially limit irradiation of the sample with the ion beam, the mask comprising an upper surface, a lower surface and a plurality of side surfaces,
  wherein the first contact surface contacts a side surface of the sample that is proximate to the optical axis of the ion beam, and the second contact surface contacts a side surface of the mask that is proximate to the optical axis of the ion beam so that the sample is partially exposed from the mask.

2. The ion milling device according to claim 1, wherein the first contact surface and the second contact surface are formed into a stepped shape.

3. The ion milling device according to claim 1, wherein the first contact surface includes two surfaces that contact different regions of the sample, and wherein a passage opening through which the ion beam passes is provided between the two surfaces of the first contact surface.

4. An ion milling sample table for an ion milling device that processes a sample by irradiating an upper surface of the sample with an ion beam emitted from an ion source, the sample table comprising:
  a shield arranged at a position that contacts the sample between the sample and the ion source, the sample further comprising a lower surface and a plurality of side surfaces, and the shield comprising an upper surface, a lower surface and a plurality of side surfaces; and
  a surface, for fixing the sample, including a first protrusion structure for holding a side surface of the sample that is proximate to an optical axis of the ion beam, a second protrusion structure for holding a side surface of the shield that is proximate to the optical axis of the ion beam, and a groove that is not directly irradiated with the ion beam that penetrates through the sample.

5. The ion milling sample table according to claim 4, wherein an irradiation area of the sample is determined according to a relative position of the first and second protrusion structures.

6. The ion milling sample table according to claim 4, wherein the sample and the shield are fixed to the sample table.

7. The ion milling sample table according to claim 4, further comprising a cap structure that can seal atmosphere.

8. The ion milling device according to claim 1, wherein the sample holder includes a cap structure that can seal atmosphere.

* * * * *